United States Patent [19]

Maurer et al.

[11] 4,155,997
[45] May 22, 1979

[54] O-ALKYL-O-[1-(TRIFLUOROMETHYL-PHENYL)-1,6-DIHYDROPYRIDAZ-(6)-ON-(3)-YL]-(THIONO)PHOSPHORIC(PHOSPHONIC) ACID ESTERS AND ESTER-AMIDES

[75] Inventors: Fritz Maurer; Hans-Jochem Riebel, both of Wuppertal; Wolfgang Behrenz, Overath-Steinenbrueck; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 824,939

[22] Filed: Aug. 15, 1977

Related U.S. Application Data

[63] Continuation of Ser. No. 615,662, Sep. 22, 1975, abandoned.

[30] Foreign Application Priority Data

Sep. 27, 1974 [DE] Fed. Rep. of Germany ....... 2446218

[51] Int. Cl.$^2$ ............................ A01N 9/36; C07F 9/65
[52] U.S. Cl. .................................. 424/200; 544/232; 544/240
[58] Field of Search .............. 260/250 AP; 544/232; 424/200

[56] References Cited

U.S. PATENT DOCUMENTS

| | | | |
|---|---|---|---|
| 2,759,937 | 8/1956 | Du Breuil | 260/250 AP |
| 3,100,206 | 8/1963 | Rigterink | 260/250 AP |
| 3,544,572 | 12/1970 | Fest et al. | 260/250 AP |
| 3,547,920 | 12/1970 | Fest et al. | 260/250 AP |
| 3,749,720 | 7/1973 | Fest et al. | 260/250 AP |
| 3,823,142 | 7/1974 | Bader et al. | 260/250 AP |
| 3,828,210 | 4/1975 | Lorenz et al. | 260/250 AP |
| 3,891,642 | 6/1975 | Lorenz et al. | 260/250 AP |

FOREIGN PATENT DOCUMENTS

| | | | |
|---|---|---|---|
| 4720025 | 12/1969 | Japan | 424/200 |

OTHER PUBLICATIONS

Du Breuil, II, J. Org. Chem. 26, pp. 3382–3386, (1961).
Yale et al., J. Med. and Pharm. Chem. 1, pp. 121, 131, (1959).
Moore "Physical Chemistry", 1962, p. 546.
Constantinides, Proc. Chem. Soc. 1964, p. 290.
Solomon et al., J. Amer. Chem. Soc. 85, (1963) 3492–3496.

*Primary Examiner*—Mark L. Berch
*Attorney, Agent, or Firm*—Sprung, Felfe, Horn, Lynch & Kramer

[57] ABSTRACT

O-alkyl-O-[1-(trifluoromethylphenyl)-1,6-dihydropyridaz-(6)-on-(3)-yl]-(thiono)phosphoric(phosphonic) acid esters and ester-amides of the formula

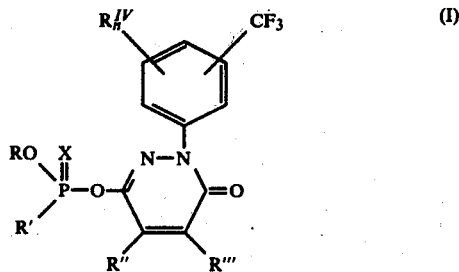

(I)

in which
R is alkyl with 1 to 6 carbon atoms,
R' is phenyl, alkyl with 1 to 4 carbon atoms, alkoxy with 1 to 6 carbon atoms, alkylthio with 1 to 6 carbon atoms or alkylamino with 1 to 4 carbon atoms in each alkyl chain,
R" and R'" each independently is hydrogen or methyl, and
$R^{IV}$ is hydrogen, halogen, nitro or halogenoalkyl with 1 to 3 carbon atoms,
n is an integer from 1 to 4, and
X is oxygen or sulfur,
which possess insecticidal and acaricidal properties.

10 Claims, No Drawings

O-ALKYL-O-[1-(TRIFLUOROMETHYLPHENYL)-1,6-DIHYDROPYRIDAZ-(6)-ON-(3)-YL]-(THIONO)-PHOSPHORIC(PHOSPHONIC) ACID ESTERS AND ESTER-AMIDES

This is a continuation of application Ser. No. 615,662, filed Sept. 22, 1975, now abandoned.

The present invention relates to and has for its objects the provision of particular new O-alkyl-O-[1-(trifluoromethylphenyl)-1,6-dihydropyridaz-(6)-on-(3)-yl]-(thiono)phosphoric(phosphonic) acid esters and ester-amides which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,759,937, published Japanese Patent Application No. 20,025/72 and Journal of Organic Chemistry, volume 26, No. 9, (1961), pages 3,382–3,386, that O,O-dialkyl-O-pyridazinyl-thionophosphoric acid esters, for example O-[1-phenyl-1,6-dihydro-6-oxo-pyridazin(3)yl]- (Compound A), O-[1-hydroxymethyl-1,6-dihydro-6-oxo-pyridazin(3)yl]- (Compound B), O-[1-(N,N-dimethylaminomethyl)-1,6-dihydro-6-oxo-pyridazin(3)yl]- (Compound C) and O-[1-(p-methylphenyl)-1,6-dihydro-6-oxo-pyridazin(3)yl]-O,O-diethylthionophosphoric acid esters (Compound D), possess insecticidal and acaricidal properties.

The present invention provides, as new compounds, the pyridazinyl(thiono)(thiol)phosphoric(phosphonic) acid esters and ester-amides of the general formula

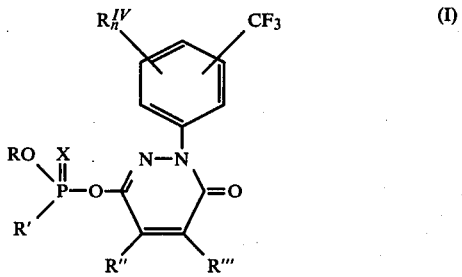

in which
R is alkyl with 1 to 6 carbon atoms,
R' is phenyl, alkyl with 1 to 4 carbon atoms, alkoxy with 1 to 6 carbon atoms, alkylthio with 1 to 6 carbon atoms or alkylamino with 1 to 4 carbon atoms in each alkyl chain,
R" and R'" each independently is hydrogen or methyl, and
$R^{IV}$ is hydrogen, halogen, nitro or halogenoalkyl with 1 to 3 carbon atoms,
n is an integer from 1 to 4, and
X is oxygen or sulfur.

Preferably R is straight-chain or branched alkyl with 1 to 5 (especially 1 to 4) carbon atoms, R' is phenyl, straight-chain or branched alkyl with 1 to 3 (especially 1 or 2) carbon atoms, straight-chain or branched alkoxy or alkylthio, each with 1 to 5 (especially 1 to 4) carbon atoms, or monoalkylamino or dialkylamino with 1 to 3 (especially 1 or 2) carbon atoms per alkyl chain, $R^{IV}$ is hydrogen, chlorine, nitro or trifluoromethyl, and n is 1, 2 or 3 (especially 1).

Surprisingly, the pyridazinyl(thiono)(thiol)phosphoric(phosphonic) acid esters and ester-amides according to the invention exhibit a better insecticidal and acaricidal action than the previously known O,O-diethyl-O-pyridazinyl-thionophosphoric acid ester derivatives of analogous structure and of the same type of action.

The new compounds are not only active against insects and mites which damage plants but are also active against pests harmful to health and pests of stored products and, in the veterinary medicine field, against animal ecto-parasites, for example parasitic fly larvae. Accordingly, they represent an enrichment of the art.

The invention also provides a process for the preparation of a pyridazinyl(thiono)(thiol)phosphoric(phosphonic) acid ester or ester-amide of the formula (I), in which a (thiono)(thiol)phosphoric(phosphonic) acid ester halide or ester-amide halide of the general formula

in which
R, R' and X have the above-mentioned meanings and Hal is halogen, is reacted with a 1-phenyl-3-hydroxy-1,6-dihydropyridazinone-(6) derivative of the general formula

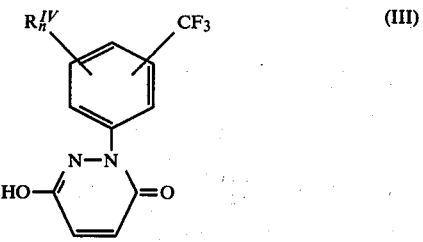

in which $R^{IV}$ and n have the above-mentioned meanings, if appropriate in the presence of a solvent or diluent, and if appropriate in the presence of an acid acceptor.

If, for example, O-ethyl-O-sec.-butyl-thonophosphoric acid diester chloride and 1-(3,5-bis-trifluoromethylphenyl)-3-hydroxy-6-oxo-pyridazine are used as starting materials, the course of the reaction can be represented by the following equation:

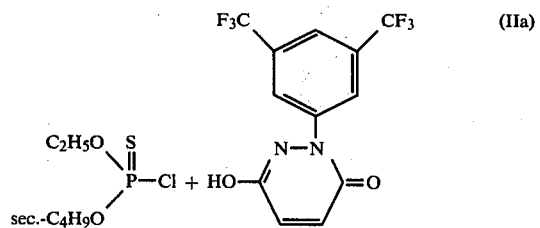

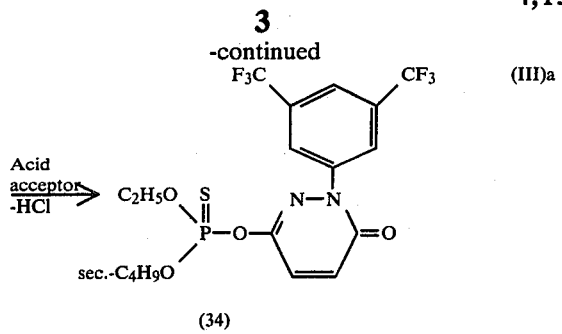

(34)

The (thiono)(thiol)phosphoric(phosphonic) acid ester halides and ester-amide halides (II) are known and can be prepared according to processes described in the literature, as can the 1-phenyl-3-hydroxy-1,6-dihydro-6-oxo-pyridazine derivatives (III), which can be prepared, for example, from the correspondingly substituted phenylhydrazines, dissolved in dilute hydrochloric acid, by reaction with maleic anhydride in accordance with the following equation:

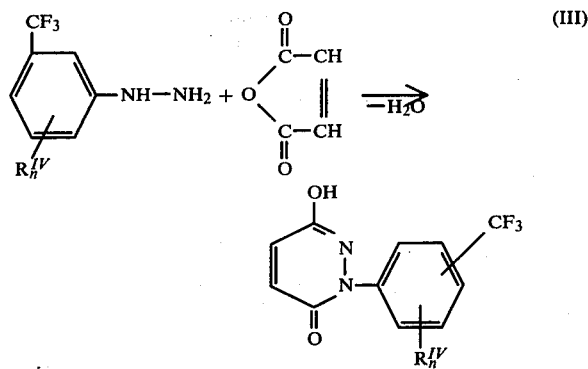

wherein $R^{IV}$ and n have the above-mentioned meanings.

The following may be mentioned as examples of (thiono)(thiol)phosphoric(phosphonic) acid ester halides and ester-amide halides to be reacted in accordance with the process: O,O-dimethyl-, O,O-diethyl-, O,O-di-n-propyl, O,O-di-isopropyl-, O,O-di-n-butyl-, O,O-di-sec.-butyl-, O,O-di-tert.-butyl-, O,O-di-isobutyl-, O,O-di-sec.-butyl-, O,O-di-tert.-butyl-, O-ethyl-O-n-propyl-, O-ethyl-O-isopropyl, O-n-butyl-O-ethyl-, O-ethyl-O-sec.-butyl- and O-ethyl-O-methyl-phosphoric acid diester chlorides and the corresponding thiono analogues; O-methyl-, O-ethyl-, O-n-propyl-, O-isopropyl-, O-n-butyl-, O-sec.-butyl-, O-isobutyl- and O-tert.-butyl-methane-, ethane-, n-propane-, isopropane- and phenylphosphonic acid ester chlorides and the corresponding thiono analogues; O,S-dimethyl, O,S-diethyl, O,S-di-n-propyl-, O,S-di-isopropyl-, O,S-di-n-butyl, O,S-di-isobutyl-, O,S-di-tert.-butyl-, O-ethyl-S-n-propyl, O-ethyl-S-isopropyl-, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thiolphosphoric acid diester chlorides and the corresponding thiono analogues; and O-methyl-N-methyl-, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl, O-n-propyl-N-n-propyl, O-isopropyl-N-n-propyl- and O-tert.-butyl-N-ethyl-phosphoric acid ester-amide chlorides, the corresponding thiono analogues and the corresponding dialkylamides.

The following may be mentioned as examples of the 1-phenyl-3-hydroxy-1,6-dihydro-6-oxo-pyridazine derivatives (III) to be employed: 1-(2- and 3-trifluoromethyl-, 3,5-bis-trifluoromethyl-, 2-trifluoromethyl-4-chloro-, 2-chloro-5-trifluoromethyl-, 2-nitro-4-trifluoromethyl- and 5-chloro-3-trifluoromethylphenyl)-3-hydroxy-1,6-dihydro-6-oxo-pyridazines, as well as the corresponding 4- and 5-methyl derivatives.

The process for the preparation of the compounds according to the invention is preferably carried out in the presence of a suitable solvent or diluent. Practically all inert organic solvents can be used for this purpose, especially aliphatic and aromatic optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles; such as acetonitrile and propionitrile.

All customary acid-binding agents can be used as acid acceptors. Alkali metal carbonates and alkali metal alcoholates, such as sodium carbonate, potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C., preferably at 40° to 60° C.

To carry out the process, the starting materials are in general employed in equimolar amounts. An excess of one or the other component in general produces no significant advantages. The reaction is preferably carried out in the presence of one of the above-mentioned solvents, if appropriate in the presence of an acid acceptor, at the indicated temperatures. After a reaction time of one or more hours, in most cases at elevated temperatures, the reaction batch is cooled to room temperature, an organic solvent, for example toluene, is added, and the organic phase is worked up in accordance with customary methods, for example washing, drying and distillation.

The new compounds are frequently obtained in the form of oils which mostly cannot be distilled without decomposition but are freed from the last volatile constituents by so-called "slight distillation", that is to say by prolonged heating under reduced pressure to moderately elevated temperatures, and are purified in this way. They are characterized by their refractive indexes. Some of the products are obtained in a crystalline form; in that case, they can be characterized by their melting points.

As has already been mentioned, the pyridazinyl(thiono)(thiol)phosphoric(phosphonic) acid esters and ester-amides according to the invention are distinguished by an excellent insecticidal and acaricidal activity. They are not only active against plant pests, pests harmful to health and pests of stored products but also, in the veterinary medicine field, against animal parasites (ectoparasites), such as parasitic fly larvae. They combine a low phyto-toxicity with a good action against both sucking and biting insects and against mites.

For this reason, the compounds according to the invention can be employed with success as pesticides in plant protection and in the hygiene field, the field of protection of stored products and the veterinary field.

The economically important pests in agriculture and forestry, as well as pests of stored products, pests destructive of materials and pests harmful to health, include: from the order of the Isopoda, for example, *Oniscus asellus, Armadillidium vulgare* and *Porcellio scaber;* from the order of the Diploda, for example, *Blaniulus guttulatus;* from the order of the Chilopoda, for example, *Geophilus carpophagus* and Scutigera spec.; from the order of the Symphyla, for example, *Scutigerella immaculata;* from the order of the Arachnida, for example, *Scorpio maurus* and *Latrodectus mactans;* from the order of the Acarina, for example, *Acarus siro, Argas reflexus, Ornithodoros moubata, Dermanyssus gallinae, Eriphyes ribis, Phyllocoptruta oleivora, Boophilus microplus, Rhipicephalus evertsi, Sarcoptes scabiei, Tarsonemus* spec., *Bryobia praetiosa, Panonychus citri, Panonychus ulmi, Tetranychus tumidus* and *Tetranychus urticae;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpha spec., *Locusta migratoria migratorioides, Melanoplus differentialis* and *Schistocerca gregaria;* from the order of the Dermaptera, for example, *Forficula auricularia;* from the order of the Isotera, for example, Reticulitermes spec.; from the order of the Anoplura, for example, *Phylloxera vastatrix,* Pemphigus spec. and *Pediculus humanus corporis;* from the order of the Thysanoptera, for example, *Hercinothrips femoralis* and *Thrips tabaci;* from the order of the Heteroptera, for example, Eurygaster spec., *Dysdercus intermedius, Piesma quadrata, Cimex lectularius, Rhodnius prolixus* and Triatoma spec.; from the order of the Homoptera, for example, *Aleurodes brassicae, Bemisia tabaci, Trialeurodes vaporariorum, Aphis gossypii, Brevicoryne brassicae, Cryptomycus ribis, Doralis fabae, Doralis pomi, Eriosoma lanigerum, Hyalopterus arundinis, Macrosiphum avenae, Myzus cerasi, Myzus persicae, Phorodon humuli, Rhosalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spec. and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Buccalatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapse pomonella,* Pieris spec., Chilo spec., *Pyrausta nubilalis, Ephestia kühniella, Galleria mellonella, Cacoecia podana, Capua reticulana, Choristoneura fumiferana, Clysia ambiguella, Homona magnanima,* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthranus spec., Attagenus spec., Lyctus spec., *Meligethes aeneus,* Ptinus spec., *Niptus hololeucus, Gibbium psylloides,* Tribolium spec., *Tenebrio molitor,* Agriotes spec., Conoderus spec., *Melolontha melolontha, Amphimallus solstitialis* and *Costelytra zealandica;* from the order of the Hymenoptera, for example Diprion spec., Hoplocampa spec., Lasius spec., *Monomorium pharaonis* and Vespa spec.; from the order of the Diptera, for example, Aēdes spec., Anopheles spec.; Culex spec., *Drosophila melanogaster, Musca domestica,* Fannia spec., *Stomoxys calcitrans,* Hypoderma spec., *Bibio hortulans, Oscinella frit,* Phormia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example, *Xenopsylla cheopis.*

When used against pests harmful to health and pests of stored products, the active compounds are distinguished by an excellent residual action on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicles assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of ready-to-use particular dosage preparations for specific application made therefrom, such as solutions, emulsions, suspensions, powders, pastes, granules, very fine capsules in polymeric substances and in coating compositions suited for use on seed, and fumigating cartridges.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
  Solvent: 3 parts by weight of acetone
  Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1

| Active compound | (*Plutella* test) Active compound concentration in % | Degree of destruction in % after 3 days |
|---|---|---|
| 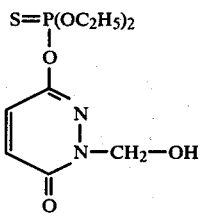 (known) (B) | 0.1<br>0.01 | 100<br>0 |

Table 1-continued (*Plutella* test)

| Active compound | Active compound concentration in % | Degree of destruction in % after 3 days |
| --- | --- | --- |
| Compound with S=P(OC₂H₅)₂ group, pyridazinone ring with N–CH₂–N(CH₃)₂ substituent (known) (C) | 0.1<br>0.01 | 100<br>0 |
| Compound (6): S=P(OCH₃)₂, pyridazinone with 3-CF₃-phenyl | 0.1<br>0.01 | 100<br>100 |
| Compound (1): S=P(OC₂H₅)₂, pyridazinone with 3-CF₃-phenyl | 0.1<br>0.01 | 100<br>100 |
| Compound (5): O=P(OC₂H₅)₂, pyridazinone with 3-CF₃-phenyl | 0.1<br>0.01 | 100<br>95 |
| Compound (3): S=P(OCH₃)(C₂H₅), pyridazinone with 3-CF₃-phenyl | 0.1<br>0.01 | 100<br>100 |
| Compound (8): S=P(OC₂H₅)(C₂H₅), pyridazinone with 3-CF₃-phenyl | 0.1<br>0.01 | 100<br>100 |

Table 1-continued
(*Plutella* test)
| Active compound | Active compound concentration in % | Degree of destruction in % after 3 days |
|---|---|---|
| 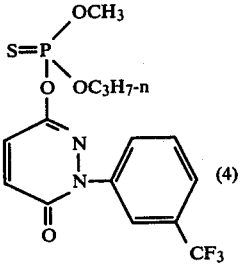 (4) | 0.1<br>0.01 | 100<br>100 |
| 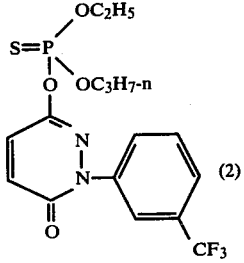 (2) | 0.1<br>0.01 | 100<br>100 |
| 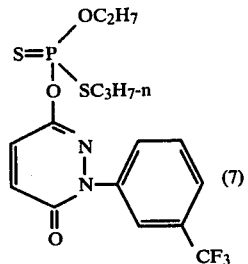 (7) | 0.1<br>0.01 | 100<br>100 |
| 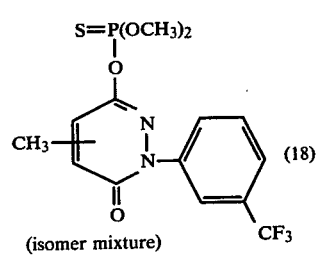 (18)<br>(isomer mixture) | 0.1<br>0.01 | 100<br>100 |
| 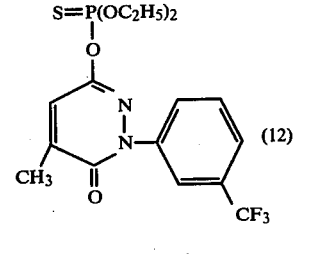 (12) | 0.1<br>0.01 | 100<br>100 |
| 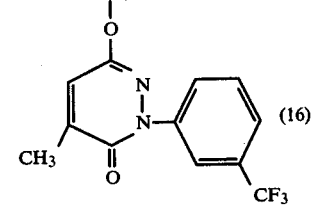 (16) | 0.1<br>0.01 | 100<br>90 |

Table 1-continued (*Plutella* test)

| Active compound | Active compound concentration in % | Degree of destruction in % after 3 days |
|---|---|---|
| Compound (14): S=P(OC$_2$H$_5$)(C$_2$H$_5$)–O– pyridazinone with CH$_3$ and 3-CF$_3$-phenyl | 0.1<br>0.01 | 100<br>100 |
| Compound (17): S=P(OC$_2$H$_5$)(SC$_3$H$_7$-n)–O– pyridazinone with CH$_3$ and 3-CF$_3$-phenyl (isomer mixture) | 0.1<br>0.01 | 100<br>100 |
| Compound (23): S=P(OC$_2$H$_5$)$_2$–O– pyridazinone with NO$_2$ and 2-CF$_3$-phenyl | 0.1<br>0.01 | 100<br>100 |
| Compound (21): S=P(OC$_2$H$_5$)(OC$_2$H$_5$)–O– pyridazinone with 3,5-(CF$_3$)$_2$-phenyl | 0.1<br>0.01 | 100<br>100 |
| Compound (25): S=P(OC$_2$H$_5$)(C$_2$H$_5$)–O– pyridazinone with 3,5-(CF$_3$)$_2$-phenyl | 0.1<br>0.01 | 100<br>100 |
| Compound (20): S=P(OC$_2$H$_5$)(OC$_2$H$_5$)–O– pyridazinone with CF$_3$ and 2-Cl-phenyl | 0.1<br>0.01 | 100<br>100 |

Table 1-continued
(Plutella test)

| Active compound | Active compound concentration in % | Degree of destruction in % after 3 days |
|---|---|---|
| (22) [structure: S=P(OC₂H₅)(C₂H₅)-O-pyridazinone-N-phenyl(CF₃)(Cl)] | 0.1<br>0.01 | 100<br>100 |
| (24) [structure: S=P(CH₃)(OC₃H₇iso)-O-pyridazinone-N-phenyl-CF₃] | 0.1<br>0.01 | 100<br>100 |
| (28) [structure: S=P(OC₃H₇-n)(C₂H₅)-O-pyridazinone-N-phenyl-CF₃] | 0.1<br>0.01 | 100<br>100 |
| (27) [structure: S=P(OC₂H₃n)(SC₃H₇-n)-O-pyridazinone-N-phenyl(CF₃)(NO₂)] | 0.1<br>0.01 | 100<br>100 |

EXAMPLE 2

Laphygma test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the degree of destruction in % was determined. 100% means that all caterpillars had been killed while 0% indicates that no caterpillars had been killed.

The active compounds, the concentrations of the active compounds, the evaluation times and the results can be seen from the table which follows:

Table 2

| Active compound | (laphygma test)<br>Active compound concentration in % | Degree of destruction in % after 3 days |
|---|---|---|
| S=P(OC₂H₅)₂-O-pyridazinone-N-CH₂-OH<br>(known) (B) | 0.1<br>0.01<br>0.001 | 100<br>40<br>0 |

Table 2-continued (*laphygma* test)

| Active compound | Active compound concentration in % | Degree of destruction in % after 3 days |
|---|---|---|
| S=P(OC$_2$H$_5$)$_2$ attached to pyridazinone with N—CH$_2$—N(CH$_3$)$_2$ (known) (C) | 0.1<br>0.01 | 100<br>0 |
| S=P(OC$_2$H$_5$)$_2$ attached to pyridazinone with N-phenyl (known) (A) | 0.1<br>0.01<br>0.001 | 100<br>100<br>0 |
| S=P(OC$_2$H$_5$)$_2$ attached to pyridazinone with N-(4-CH$_3$-phenyl) (known) (D) | 0.1<br>0.01<br>0.001 | 100<br>100<br>0 |
| S=P(OC$_2$H$_5$)$_2$ attached to pyridazinone with N-(3-CF$_3$-phenyl) (1) | (1)<br>0.1<br>0.01<br>0.001 | 100<br>100<br>95 |
| S=P(OCH$_3$)(OC$_3$H$_7$-n) attached to pyridazinone with N-(3-CF$_3$-phenyl) (4) | (4)<br>0.1<br>0.01<br>0.001 | 100<br>100<br>100 |
| S=P(OC$_3$H$_7$-n)(OC$_2$H$_5$) attached to pyridazinone with N-(3-CF$_3$-phenyl) (28) | (28)<br>0.1<br>0.01<br>0.001 | 100<br>100<br>100 |

EXAMPLE 3

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3

(*Myzus* test)

| Active compound in % | Active compound concentration after 1 day | Degree of destruction in % |
|---|---|---|
| S=P(OC$_2$H$_5$)$_2$ attached to pyridazinone with N—CH$_2$—OH (known) (B) | 0.1<br>0.01<br>0.001 | 100<br>75<br>0 |
| S=P(OC$_2$H$_5$)$_2$ attached to pyridazinone with N—CH$_2$—N(CH$_3$)$_2$ (known) (C) | 0.1<br>0.01<br>0.001 | 100<br>50<br>0 |
| S=P(OC$_2$H$_5$)$_2$ attached to pyridazinone with N-phenyl (known) (A) | 0.1<br>0.01<br>0.001 | 100<br>95<br>0 |
| S=P(OC$_2$H$_5$)$_2$ attached to pyridazinone with N-(4-CH$_3$-phenyl) (known) (D) | 0.1<br>0.01<br>0.001 | 100<br>95<br>0 |

Table 3-continued
(Myzus test)

| Active compound in % | Active compound concentration after 1 day | Degree of destruction in % |
|---|---|---|
| Structure: S=P(OCH₃)(OC₂H₅)-O-[pyridazinone-N-(3-CF₃-phenyl)] (3) | 0.1 | 100 |
| | 0.01 | 99 |
| | 0.001 | 98 |
| Structure: S=P(OC₂H₅)(C₂H₅)-O-[pyridazinone-N-(3-CF₃-phenyl)] (8) | 0.1 | 100 |
| | 0.01 | 100 |
| | 0.001 | 100 |

EXAMPLE 4

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4
(Tetranychus test)

| Active compound | Active compound concentration in % | Degree of destruction in % after 2 days |
|---|---|---|
| S=P(OC₂H₅)₂-O-[pyridazinone-N-CH₂-OH] (known) (B) | 0.1 | 95 |
| | 0.01 | 0 |
| S=P(OC₂H₅)₂-O-[pyridazinone-N-CH₂-N(CH₃)₂] (known) (C) | 0.1 | 90 |
| | 0.01 | 0 |
| S=P(OC₂H₅)₂-O-[pyridazinone-N-phenyl] (known) (A) | 0.1 | 98 |
| | 0.01 | 0 |
| S=P(OC₂H₅)₂-O-[pyridazinone-N-(4-CH₃-phenyl)] (known) (D) | 0.1 | 40 |
| | 0.01 | 0 |
| S=P(OCH₃)₂-O-[pyridazinone-N-(3-CF₃-phenyl)] (6) | 0.1 | 100 |
| | 0.01 | 95 |
| S=P(OC₂H₅)₂-O-[pyridazinone-N-(3-CF₃-phenyl)] (1) | 0.1 | 100 |
| | 0.01 | 70 |
| S=P(OCH₃)(OC₂H₅)-O-[pyridazinone-N-(3-CF₃-phenyl)] (3) | 0.1 | 100 |
| | 0.01 | 100 |

Table 4-continued
(*Tetranychus* test)

| Compound | Active compound concentration in % | Degree of destruction in % after 2 days |
|---|---|---|
| (8) ![structure with OC₂H₅, S=P, O-C₂H₅, pyridazinone with m-CF₃ phenyl] | 0.1<br>0.01 | 100<br>100 |
| (14) ![structure with OC₂H₅, S=P, C₂H₅, CH₃-pyridazinone with m-CF₃ phenyl] | 0.1<br>0.01 | 100<br>100 |
| (23) ![structure S=P(OC₂H₅)₂, pyridazinone with 2-NO₂, 4-CF₃ phenyl] | 0.1<br>0.01 | 100<br>95 |
| (24) ![structure with CH₃, S=P, OC₃H₇iso, pyridazinone with m-CF₃ phenyl] | 0.1<br>0.01<br>0.001 | 100<br>99<br>95 |

EXAMPLE 5

LD₁₀₀ test
  Test insects *Sitophilus granarius*
  Solvent: Acetone 2 parts by weight of the active compound were taken up in 1,000 parts by volume of the solvent. The solution so obtained was diluted with further solent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all the test insects had been killed; 0% denotes that no test insects had been killed.

The active compounds, the concentrations of the active compounds, the test insects and the results can be seen from the following table:

Table 5
(LD₁₀₀ test/*Sitophilus granarius*)

| Active compound | Active compound concentration in % | Degree of destruction in % |
|---|---|---|
| (known) (C) ![S=P(OC₂H₅)₂, pyridazinone N-CH₂-N(CH₃)₂] | 0.2 | 0 |
| (known) (B) ![S=P(OC₂H₅)₂, pyridazinone N-CH₂-OH] | 0.2 | 90 |
| (known) (A) ![S=P(OC₂H₅)₂, pyridazinone N-phenyl] | 0.2<br>0.02 | 100<br>0 |
| (1) ![S=P(OC₂H₅)₂, pyridazinone with m-CF₃ phenyl] | 0.2<br>0.02 | 100<br>100 |
| (3) ![S=P with OCH₃, C₂H₅, pyridazinone with m-CF₃ phenyl] | 0.2<br>0.02 | 100<br>100 |
| (4) ![S=P with OCH₃, OC₃H₇-n, pyridazinone with m-CF₃ phenyl] | 0.2<br>0.02 | 100<br>100 |

Table 5-continued
(LD$_{100}$ test/*Sitophilus granarius*)

| Active compound | Active compound concentration in % | Degree of destruction in % |
|---|---|---|
| (8) structure: S=P(OC$_2$H$_5$)(OC$_2$H$_5$) — O — pyridazinone-N-phenyl-CF$_3$ | 0.2 / 0.02 | 100 / 100 |
| (14) structure: with CH$_3$ on ring | 0.2 / 0.02 | 100 / 100 |
| (23) structure: S=P(OC$_2$H$_5$)$_2$—O— pyridazinone with NO$_2$ and CF$_3$ | 0.2 / 0.02 | 100 / 100 |
| (5) structure: O=P(OC$_2$H$_5$)$_2$—O— pyridazinone-CF$_3$ | 0.2 / 0.02 | 100 / 100 |

EXAMPLE 6

LT$_{100}$ test for Diptera
Test insects: *Aëdes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 6
(LT$_{100}$ test for diptera/*Aedes aegypti*)

| Active compound | Active compound concentration in the solution, in % | LT$_{100}$ in minutes (') or hours (hrs) |
|---|---|---|
| (known) (B): S=P(OC$_2$H$_5$)$_2$—O— pyridazinone-N-CH$_2$-OH | 0.2 / 0.02 | 180' / 3 hrs 0% |
| (known) (A): S=P(OC$_2$H$_5$)$_2$—O— pyridazinone-N-phenyl | 0.2 / 0.02 | 120' / 3 hrs 0% |
| (8): S=P(OC$_2$H$_5$)(OC$_2$H$_5$)—O— pyridazinone-N-phenyl-CF$_3$ | 0.2 / 0.02 | 120' / 180' |
| (3): S=P(OCH$_3$)(OC$_2$H$_5$)—O— pyridazinone-N-phenyl-CF$_3$ | 0.2 / 0.02 / 0.002 | 120' / 120' / 3 hrs 70% |
| (23): S=P(OC$_2$H$_5$)$_2$—O— pyridazinone with NO$_2$ and CF$_3$ | 0.2 / 0.02 / 0.002 | 60' / 120' / 180' |

EXAMPLE 7

LT$_{100}$ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 7

($LT_{100}$ test for diptera/*Musca domestica*)

| Active compound | Active compound concentration in the solution, in % | $LT_{100}$ in minutes (') or hours (hrs) |
|---|---|---|
| S=P(OC₂H₅)₂ structure with CH₃ (known) (D) | 0.2<br>0.02 | 60'<br>6 hrs |
| S=P(OC₂H₅)₂ structure phenyl (known) (A) | 0.2<br>0.02 | 100'<br>6 hrs |
| S=P(OC₂H₅)₂ structure with NO₂, CF₃ (23) | 0.2<br>0.02 | 30'<br>80' |

EXAMPLE 8

Test with parasitic fly larvae
Solvent:
35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained about 2 cm³ of horse muscle. 0.5 ml of the preparation of active compound was applied to this horse meat. After 24 hours, the degree of destruction in % was determined. 100% means that all the larvae had been killed and 0% means that no larvae had been killed.

The active compounds investigated, the concentrations of the active compounds used and the results obtained can be seen from the table which follows:

Table 8

(Test with parasitic fly larvae/*Lucilia cuprina* res.)

| Active compound | Active compound concentration in ppm | Degree of destruction in % |
|---|---|---|
| (4) structure with OCH₃, OC₃H₇-n, CF₃ | 100<br>30<br>10 | 100<br>100<br>100 |
| (12) structure S=P(OC₂H₅)₂, CH₃, CF₃ | 100<br>30 | 100<br>>50 |
| (8) structure with OC₂H₅, C₂H₅, CF₃ | 100<br>30 | 100<br>>50 |
| (14) structure with OC₂H₅, C₂H₅, CH₃, CF₃ | 100<br>30<br>10 | 100<br>100<br>100 |
| (18) S=P(OCH₃)₂, CH₃, CF₃ (isomer mixtrure) | 100<br>30<br>10 | 100<br>100<br>100 |

The process of this invention is illustrated in the following preparative examples:

EXAMPLE 9

(a) The 1-phenyl-3-hydroxy-6-oxo-pyridazine derivatives (III) required as starting materials can be prepared, for example, as follows:

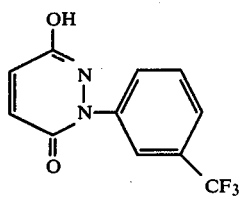
(IIIb)

176 g (1 mole) of 3-trifluoromethylphenyl-hydrazine (for preparation, see German Published Specification DAS No. 1,116,534) were dissolved in a mixture of 1,000 ml of water and 250 ml of concentrated hydrochloric acid and then 98 g (1 mole) of maleic anhydride were added at about 90° C. The mixture was then stirred for a further hour at 95°–100° C. and, after the reaction mixture had cooled, the product which had crystallized out was filtered off. It could be purified by dissolving it in dilute sodium hydroxide solution and reprecipitating with hydrochloric acid. This gave 210 g (82% of theory) of 1-(3-trifluoromethylphenyl)-3-hydroxy-1,6-dihydropyridazinone-(6) in the form of a pale yellow-colored powder of melting point 176° C.

The following compounds could be prepared analogously:

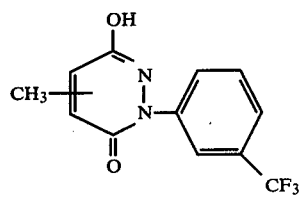
88% yield; melting point 245° C. (IIId)

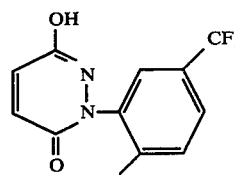
65% yield; melting point 230° C. (IIId)

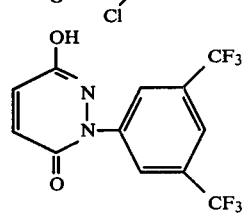
69% yield; melting point 174° C. (IIIa)

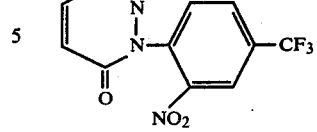
40% yield; melting point 208° C. (IIIe)

b) 
$S=P(OC_2H_5)_2$

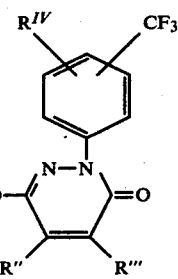
(I)

A mixture of 25.6 g (0.1 mole) of 1-(3-trifluoromethylphenyl)-3-hydroxy-1,6-dihydropyridazinone-(6), 20.7 g (0.15 mole) of potassium carbonate, 18.8 g (0.1 mole) of O,O-diethylthionophosphoric acid diester chloride and 300 ml of acetonitrile was stirred for 4 hours at 50° C. It was then cooled to room temperature and, after addition of 400 ml of toluene, was extracted by shaking twice with 300 ml of water. The organic phase was separated off, dried over sodium sulfate and freed from the solvent in vacuo. The residue was subjected to slight distillation. This gave 33.4 g (82% of theory) of O,O-diethyl-O-[1-(3-trifluoromethylphenyl)-1,6-dihydropyridaz-(6)-on-(3)-yl]-thionophosphoric acid ester in the form of a yellow oil having a refractive index $n_D^{22}$ of 1.5240.

The following compounds of the formula (I)

could be prepared analogously:

| Compound No. | R | R' | R'' | R''' | $R^{IV}$ | Position of CF$_3$ group | X | Yield (% of theory) | Physical data (refractive index, melting point °C.) |
|---|---|---|---|---|---|---|---|---|---|
| 2 | —C$_2$H$_5$ | —OC$_3$H$_7$-n | H | H | H | 3 | S | 71 | $n_D^{21}$:1.5212 |
| 3 | —CH$_3$ | —C$_2$H$_5$ | H | H | H | 3 | S | 65 | $n_D^{21}$:1.5413 |
| 4 | —CH$_3$ | —OC$_3$H$_7$-n | H | H | H | 3 | S | 87 | $n_D^{21}$:1.5290 |
| 5 | —C$_2$H$_5$ | —OC$_2$H$_5$ | H | H | H | 3 | O | 74 | $n_D^{26}$:1.4946 |
| 6 | —CH$_3$ | —OCH$_3$ | H | H | H | 3 | S | 61 | 58 |
| 7 | —C$_2$H$_5$ | —SC$_3$H$_7$-n | H | H | H | 3 | S | 53 | $n_D^{26}$:1.5475 |
| 8 | —C$_2$H$_5$ | —C$_2$H$_5$ | H | H | H | 3 | S | 56 | $n_D^{24}$:1.5338 |
| 9 | —C$_2$H$_5$ | —C$_6$H$_5$ | H | H | H | 3 | S | 40 | $n_D^{24}$:1.5741 |
| 10 | —C$_2$H$_5$ | —NH—C$_3$H$_7$-iso | H | H | H | 3 | S | 30 | $n_D^{24}$:1.5303 |
| 11 | —C$_2$H$_5$ | —OC$_2$H$_5$ | CH$_3$ | H | H | 3 | S | 76 | 86 |
| 12 | —C$_2$H$_5$ | —OC$_2$H$_5$ | H | CH$_3$ | H | 3 | S | 66 | $n_D^{20}$:1.5251 |
| 13 | —C$_2$H$_5$ | —C$_2$H$_5$ | CH$_3$ | H | H | 3 | S | 62 | 80 |
| 14 | —C$_2$H$_5$ | —C$_2$H$_5$ | H | CH$_3$ | H | 3 | S | 84 | $n_D^{20}$:1.5385 |

-continued

| Compound No. | R | R' | R" | R'" | R^{IV} | Position of CF$_3$ group | X | Yield (% of theory) | Physical data (refractive index, melting point ° C.) |
|---|---|---|---|---|---|---|---|---|---|
| 15 | —C$_2$H$_5$ | —OC$_2$H$_5$ | CH$_3$ | H | H | 3 | O | 64 | 72 |
| 16 | —C$_2$H$_5$ | —OC$_2$H$_5$ | H | CH$_3$ | H | 3 | O | 84 | $n_D^{20}$:1.4987 |
| 17 | —C$_2$H$_5$ | —SC$_3$H$_7$-n | CH$_3$ / H | H / CH$_3$ | H | 3 | S | 86 | $n_D^{20}$:1.5486 (isomer mixture) |
| 18 | —CH$_3$ | —OCH$_3$ | CH$_3$ / H | H / CH$_3$ | H | 3 | S | 54 | $n_D^{24}$:1.5375 (isomer mixture) |
| 19 | —CH$_3$ | —OC$_3$H$_7$-n | CH$_3$ / H | H / CH$_3$ | H | 3 | S | 59 | $n_D^{24}$:1.5300 |
| 20 | —C$_2$H$_5$ | —OC$_2$H$_5$ | H | H | 6-Cl | 3 | S | 41 | $n_D^{24}$:1.5330 |
| 21 | —C$_2$H$_5$ | —OC$_2$H$_5$ | H | H | 5-CF$_3$ | 3 | S | 72 | $n_D^{24}$:1.5009 |
| 22 | —C$_2$H$_5$ | —C$_2$H$_5$ | H | H | 6-Cl | 3 | S | 70 | $n_D^{25}$:1.5473 |
| 23 | —C$_2$H$_5$ | —OC$_2$H$_5$ | H | H | 2-NO$_2$ | 4 | S | 38 | $n_D^{22}$:1.5431 |
| 24 | —C$_3$H$_7$-iso | —CH$_3$ | H | H | H | 3 | S | 63 | $n_D^{25}$:1.5348 |
| 25 | —C$_2$H$_5$ | —C$_2$H$_5$ | H | H | 5-CF$_3$ | 3 | S | 44 | $n_D^{23}$:1.5084 |
| 26 | —C$_2$H$_5$ | —SC$_3$H$_7$-n | H | H | 5-CF$_3$ | 3 | S | 46 | $n_D^{23}$:1.5185 |
| 27 | —C$_2$H$_5$ | —SC$_3$H$_7$-n | H | H | 2-NO$_2$ | 4 | S | 80 | $n_D^{26}$:1.5332 |
| 28 | —C$_3$H$_7$-n | —C$_2$H$_5$ | H | H | H | 3 | S | 62 | $n_D^{24}$:1.5277 |
| 29 | —C$_3$H$_7$-iso | —C$_3$H$_7$-iso | H | H | H | 3 | S | 60 | $n_D^{23}$:1.5173 |

Other compounds which can be similarly prepared include:

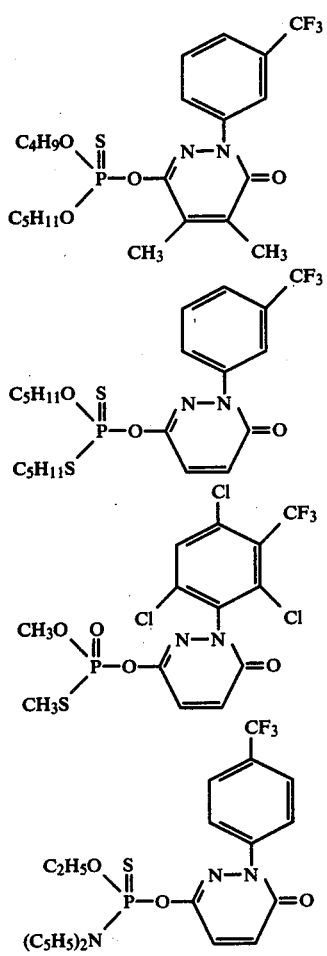

and the like.

It will be appreciated that the instant specification and examples are set forth by way of illustration and not limitation, and that various modifications and changes may be made without departing from the spirit and scope of the present invention.

What is claimed is:

1. A pyridazinyl(thiono)(thiol)phosphoric(phosphonic) acid ester or ester-amide of the formula

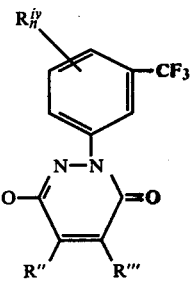

in which
R is alkyl with 1 to 6 carbon atoms,
R' is phenyl, alkyl with 1 to 4 carbon atoms, alkoxy with 1 to 6 carbon atoms, alkylthio with 1 to 6 carbon atoms or alkylamino with 1 to 4 carbon atoms in each alkyl chain,
R" and R'" each independently is hydrogen or methyl,
R$^{IV}$ is hydrogen, halogen, nitro or trifluoromethyl,
n is an integer from 1 to 4, and
X is oxygen or sulfur.

2. A compound according to claim 1, in which R is alkyl with 1 to 5 carbon atoms, R' is phenyl, alkyl with 1 to 3 carbon atoms, alkoxy or alkylthio with 1 to 5 carbon atoms, or alkylamino with 1 to 3 carbon atoms per alkyl chain, R$^{IV}$ is hydrogen, chlorine, nitro or trifluoromethyl, and n is 1, 2 or 3.

3. The compound according to claim 1 wherein such compound is O-methyl-O-[1-(3-trifluoromethylphenyl)-1,6-dihydropyridaz-(6)-on-(3)yl]-ethanethionophosphonic acid ester of the formula 4. The compound according to claim 1 wherein such compound is O,O-diethyl-O-[1-(3-trifluoromethylphenyl)-1,6-dihydropyridaz-(6)-on-(3)yl]-phosphoric acid ester of the formula

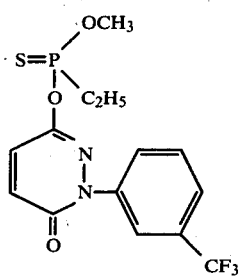

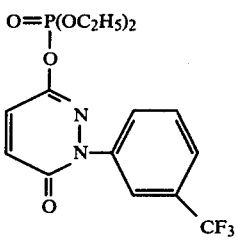

5. The compound according to claim 1 wherein such compound is O,O-dimethyl-O-[1-(3-trifluoromethylphenyl)-1,6-dihydropyridaz-(6)-on-(3)yl]-thionophosphoric acid ester of the formula

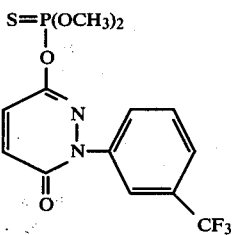

6. The compound according to claim 1 wherein such compound is O-ethyl-O-[1-(3-trifluoromethylphenyl)-1,6-dihydropyridaz-(6)-on-(3)yl]-ethanethionophosphonic acid ester of the formula

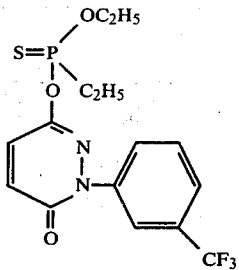

7. The compound according to claim 1 wherein such compound is O-isopropyl-O-[1-(3-trifluoromethylphenyl)-1,6-dihydropyridaz-(6)-on-(3)yl]-methanethionophosphonic acid ester of the formula

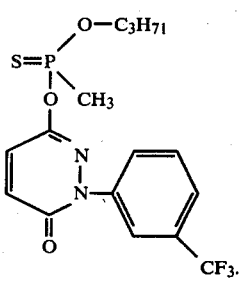

8. An insecticidal or acaricidal composition containing as active ingredient an insecticidally or acaricidally effective amount of a compound according to claim 1 in admixture with a diluent.

9. A method of combating insects or acarids selected from the group consisting of *Musca domestica*, *Aëdes aegypti*, *Plutella*, *Laphygma*, *Myzus*, *Tetranychus*, *Sitophilus granarius* and *Lucilia cuprina* which comprises applying to the insects or acarids or to a habitat thereof an insecticidally or acaricidally effective amount of a compound according to claim 1.

10. The method according to claim 9 in which said compound is
   O-methyl-O-[1-(3-trifluoromethylphenyl)-1,6-dihydropyridaz-(6)-on-(3)yl]-ethanethionophosphonic acid ester,
   O,O-diethyl-O-[1-(3-trifluoromethylphenyl)-1,6-dihydropyridaz-(6)-on-(3)yl]-phosphoric acid ester,
   O,O-dimethyl-O-[1-(3-trifluoromethylphenyl)-1,6-dihydropyridaz-(6)-on-(3)yl]-thionophosphoric acid ester,
   O-ethyl-O-[1-(3-trifluoromethylphenyl)-1,6-dihydropyridaz-(6)-on-(3)yl]-ethanethionophosphonic acid ester, or
   O-isopropyl-O-[1-(3-trifluoromethylphenyl)-1,6-dihydropyridaz-(6)-on-(3)yl]-methanethionophosphonic acid ester.

* * * * *

UNITED STATES PATENT AND TRADEMARK OFFICE
CERTIFICATE OF CORRECTION

PATENT NO. : 4,155,997
DATED : May 22, 1979
INVENTOR(S) : Maurer et al

It is certified that error appears in the above–identified patent and that said Letters Patent are hereby corrected as shown below:

Col. 32  Line 18   "$O-C_3H_{71}$" should be --$O-C_3H_{71}$--.

Signed and Sealed this

Ninth Day of October 1979

[SEAL]

Attest:

RUTH C. MASON
Attesting Officer

LUTRELLE F. PARKER
Acting Commissioner of Patents and Trademarks